(12) United States Patent
Huffman et al.

(10) Patent No.: US 8,770,030 B2
(45) Date of Patent: *Jul. 8, 2014

(54) ULTRASONIC TRANSMITTER AND RECEIVER WITH COMPLIANT MEMBRANE

(75) Inventors: James D. Huffman, Pittsford, NY (US); Gary A. Kneezel, Webster, NY (US)

(73) Assignee: Eastman Kodak Company, Rochester, NY (US)

( * ) Notice: Subject to any disclaimer, the term of this patent is extended or adjusted under 35 U.S.C. 154(b) by 592 days.

This patent is subject to a terminal disclaimer.

(21) Appl. No.: 13/089,513

(22) Filed: Apr. 19, 2011

(65) Prior Publication Data

US 2012/0269031 A1 Oct. 25, 2012

(51) Int. Cl.
*G01N 29/04* (2006.01)

(52) U.S. Cl.
USPC ................................. 73/627; 73/514.36

(58) Field of Classification Search
USPC ............... 73/627, 514.29, 514.34, 514.36; 310/329
See application file for complete search history.

(56) References Cited

U.S. PATENT DOCUMENTS

| | | | |
|---|---|---|---|
| 6,474,787 B1 | 11/2002 | Cruz-Uribe | |
| 6,540,339 B2 * | 4/2003 | Cruz-Uribe | 347/70 |
| 6,857,501 B1 | 2/2005 | Han et al. | |
| 7,571,992 B2 | 8/2009 | Jia et al. | |
| 7,712,368 B2 * | 5/2010 | Sugiura et al. | 73/602 |
| 8,409,900 B2 * | 4/2013 | Huffman et al. | 438/50 |
| 8,434,855 B2 * | 5/2013 | Huffman et al. | 347/54 |
| 2005/0242687 A1 | 11/2005 | Kawakubo et al. | |
| 2009/0107243 A1 | 4/2009 | Sugiura et al. | |

* cited by examiner

*Primary Examiner* — J M Saint Surin
(74) *Attorney, Agent, or Firm* — William R. Zimmerli

(57) ABSTRACT

An ultrasonic transmitter and receiver includes a MEMS composite transducer. The MEMS composite transducer includes a substrate. Portions of the substrate define an outer boundary of a cavity. A first MEMS transducing member includes a first size. A first portion of the first MEMS transducing member is anchored to the substrate. A second portion of the first MEMS transducing member extends over at least a portion of the cavity and is free to move relative to the cavity. A second MEMS transducing member includes a second size that is smaller than the first size of the first MEMS transducing member. A first portion of the second MEMS transducing member is anchored to the substrate. A second portion of the second MEMS transducing member extends over at least a portion of the cavity and is free to move relative to the cavity. A compliant membrane is positioned in contact with the first and second MEMS transducing members. A first portion of the compliant membrane covers the first and second MEMS transducing members. A second portion of the compliant membrane is anchored to the substrate.

28 Claims, 13 Drawing Sheets

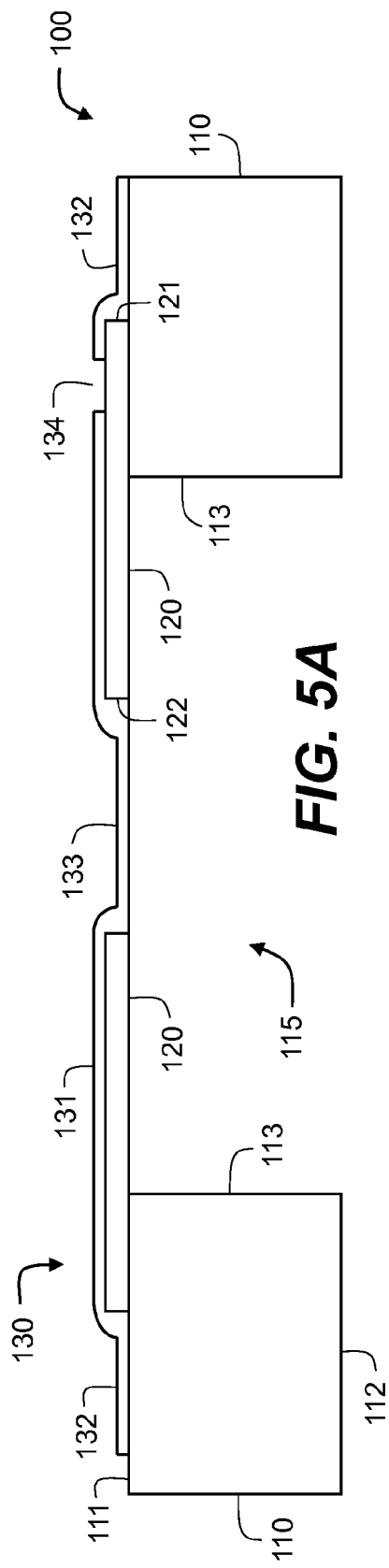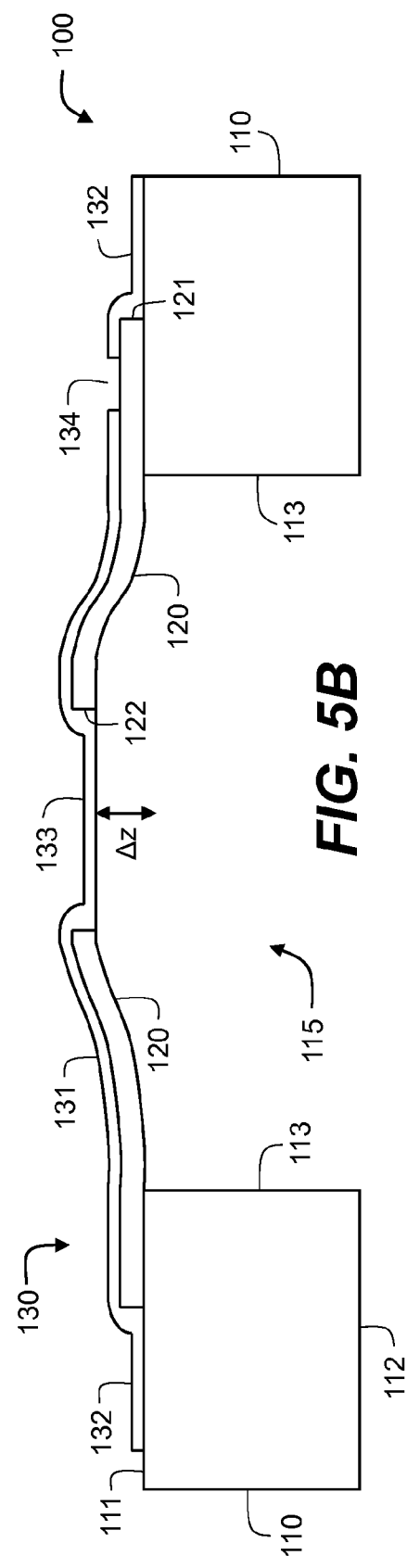

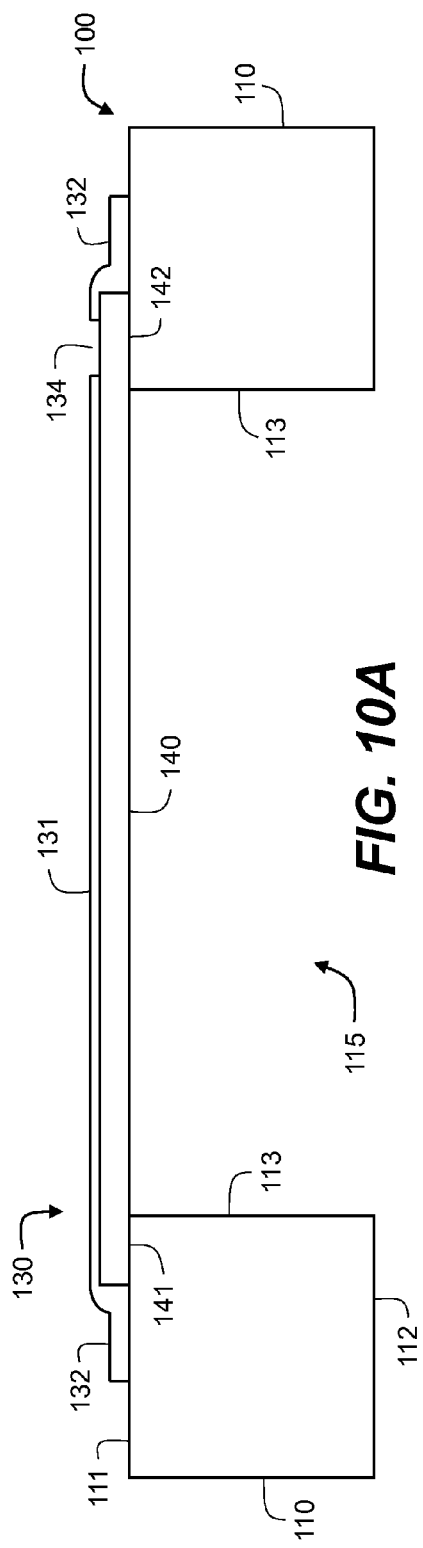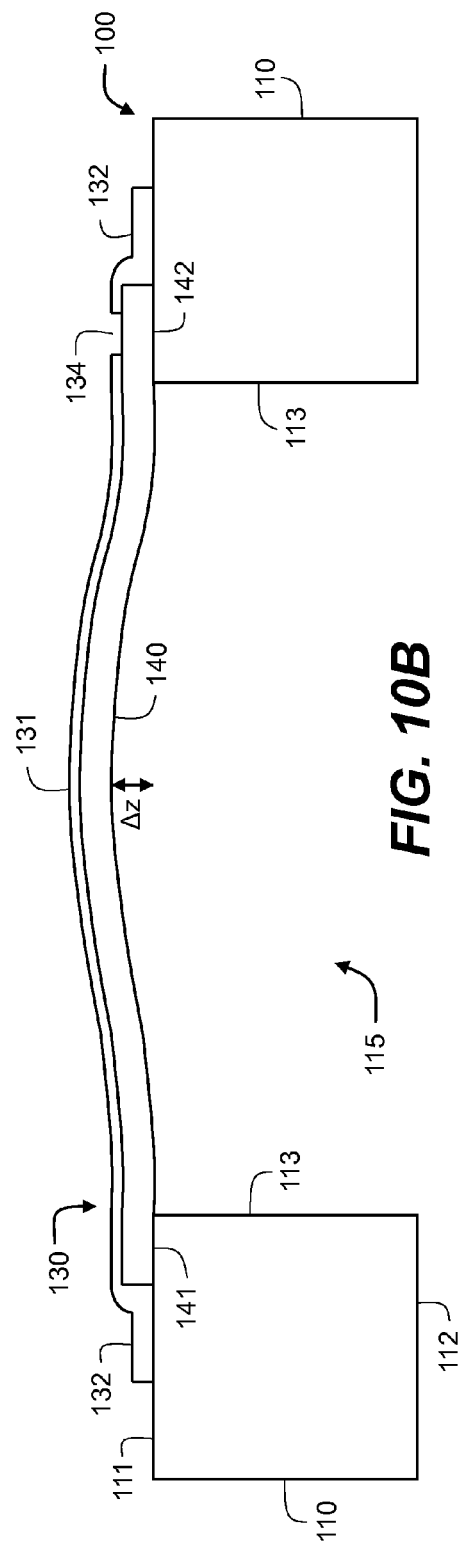

US 8,770,030 B2

ULTRASONIC TRANSMITTER AND RECEIVER WITH COMPLIANT MEMBRANE

CROSS REFERENCE TO RELATED APPLICATIONS

Reference is made to commonly-assigned, U.S. patent application Ser. No. 13/089,541, entitled "MEMS COMPOSITE TRANSDUCER INCLUDING COMPLIANT MEMBRANE", Ser. No. 13/089,532, entitled "FABRICATING MEMS COMPOSITE TRANSDUCER INCLUDING COMPLIANT MEMBRANE", Ser. No. 13/089,524, entitled "METHOD OF OPERATING AN ULTULTRASONIC TRANSMITTER AND RECEIVER", all filed concurrently herewith.

FIELD OF THE INVENTION

This invention relates generally to ultrasonic transducers and ultrasonic imaging systems, and in particular to MEMS-based ultrasonic transmitters and receivers.

BACKGROUND OF THE INVENTION

Micro-Electro-Mechanical Systems (or MEMS) devices are becoming increasingly prevalent as low-cost, compact devices having a wide range of applications. Uses include pressure sensors, accelerometers, gyroscopes, microphones, digital mirror displays, microfluidic devices, biosensors, chemical sensors, and others.

MEMS transducers include both actuators and sensors. In other words they typically convert an electrical signal into a motion, or they convert a motion into an electrical signal. They are typically made using standard thin film and semiconductor processing methods. As new designs, methods and materials are developed, the range of usages and capabilities of MEMS devices can be extended.

MEMS transducers are typically characterized as being anchored to a substrate and extending over a cavity in the substrate. Three general types of such transducers include a) a cantilevered beam having a first end anchored and a second end cantilevered over the cavity; b) a doubly anchored beam having both ends anchored to the substrate on opposite sides of the cavity; and c) a clamped sheet that is anchored around the periphery of the cavity. Type c) is more commonly called a clamped membrane, but the word membrane will be used in a different sense herein, so the term clamped sheet is used to avoid confusion.

Sensors and actuators can be used to sense or provide a displacement or a vibration. For example, the amount of deflection $\delta$ of the end of a cantilever in response to a stress $\sigma$ is given by Stoney's formula $$\delta = 3\sigma(1-v)L^2/1Et^2 \quad (1),$$

where v is Poisson's ratio, E is Young's modulus, L is the beam length, and t is the thickness of the cantilevered beam. In order to increase the amount of deflection for a cantilevered beam, one can use a longer beam length, a smaller thickness, a higher stress, a lower Poisson's ratio, or a lower Young's modulus. The resonant frequency of vibration of an undamped cantilevered beam is given by $$f = \omega_0/2\pi = (k/m)^{1/2}/2\pi \quad (2),$$

where k is the spring constant and m is the mass. For a cantilevered beam of constant width w, the spring constant k is given by $$k = Ewt^3/4L^3 \quad (3).$$

It can be shown that the dynamic mass m of an oscillating cantilevered beam is approximately one quarter of the actual mass of $\rho wtL$ ($\rho$ being the density of the beam material), so that within a few percent, the resonant frequency of vibration of an undamped cantilevered beam is approximately $$f \sim (t/2\pi L^2)(E/\rho)^{1/2} \quad (4).$$

For a lower resonant frequency one can use a smaller Young's modulus, a smaller thickness, a longer length, or a larger density. A doubly anchored beam typically has a lower amount of deflection and a higher resonant frequency than a cantilevered beam having comparable geometry and materials. A clamped sheet typically has an even lower amount of deflection and an even higher resonant frequency.

Based on material properties and geometries commonly used for MEMS transducers the amount of deflection can be limited, as can the frequency range, so that some types of desired usages are either not available or do not operate with a preferred degree of energy efficiency, spatial compactness, or reliability. In addition, typical MEMS transducers operate independently. For some applications, independent operation of MEMS transducers is not able to provide the range of performance desired.

Ultrasonic imaging is an important analytical tool and, as such, is useful in several applications, including, for example, medical diagnostics and nondestructive testing. It is a noninvasive and benign way of imaging features that are below the surface of an object and therefore not readily observable by optical methods. Ultrasonic waves are sent into an object, echo signals are received, and an image is obtained by analyzing and interpreting the echo signals. For medical ultrasonography the frequency of the ultrasonic pulses typically ranges from around 1 MHz to around 20 MHz, with the lower frequencies in this range being used to image organs or other structures deep within the body, and the higher frequencies being used to image structures (in greater detail) that are closer to the surface.

Ultrasonic waves are typically produced by a piezoelectric transducer array housed in a probe. Electrical pulses from a pulse source cause the piezoelectric transducers in the array to oscillate. By controlling the timing of pulsing of various transducers in the array, an arc-shaped wave front can be provided in a process that is sometimes called beam forming. The ultrasonic wave travels into the object and comes into focus at a desired depth. Impedance matching materials on the face of the piezoelectric transducer array probe enable the waves to be transmitted efficiently into the object.

For medical ultrasonography a water-based gel is typically placed between the patient's skin and the probe to promote efficient transmission of waves and reception of echoes. The ultrasonic wave is partially reflected from the layers between different tissues. In particular, the ultrasonic wave is reflected anywhere there are density changes. The reflected ultrasonic echo induces one or more transducers in the array to vibrate. There is typically significant attenuation of the ultrasonic wave as it passes through the object and is reflected, so that the reflected wave (the echo) has a much lower amplitude than the ultrasonic wave that was sent into the object. The transducers convert the reflected waves into electrical signals that are amplified and sent to a controller for processing and transforming into a digital image.

In a conventional ultrasonic transducer array, the same transducers are used for both transmitting waves into the object and receiving reflected waves. A block diagram of a portion of a conventional ultrasonic imaging system 10 is shown in FIG. 1. A controller 30 includes circuitry for controlling electrical pulses to be sent to the transducers of ultrasonic transducer array 20. Pulsing circuitry 40 includes a high voltage power supply, a pulse generator, and a high voltage amplifier for providing electrical pulses having an amplitude typically between 20V and 200V. The high voltage pulses are selectively passed through a transmit/receive switch 25 to ultrasonic transducer array 20. Reflected waves are converted to echo electrical signals by ultrasonic transducer array 20 and are selectively passed through transmit/receive switch 25 to receiver circuitry 45. Receiver circuitry 45 includes a low noise amplifier to amplify the echo electrical signals. The amplified echo signals are sent to signal processing circuitry in the controller 30 for processing the echo signals and transforming them into a digital image. The image can be viewed on display 36, saved in storage 38, or printed on a printing system (not shown).

The purpose of the transmit/receive switch 25 is primarily to isolate receiver circuitry 45 from pulse circuitry 40. Since the pulse circuitry 40 is otherwise connected to receiver circuitry 45 at transducer array 20, high voltage signals from pulse circuitry 40 may damage the low noise amplifier or other sensitive components of the receiver circuitry.

Accordingly, there is a need for a MEMS transducer design and method of operation that enables low cost and spatially compact transducer arrays for ultrasonic transmitters and receivers, such that the transmitter portion of the transducer is electrically isolated from the receiver portion, thereby reducing or even eliminating the need for a transmit/receive switch.

SUMMARY OF THE INVENTION

According to one aspect of the invention, an ultrasonic transmitter and receiver includes a MEMS composite transducer. The MEMS composite transducer includes a substrate. Portions of the substrate define an outer boundary of a cavity. A first MEMS transducing member includes a first size. A first portion of the first MEMS transducing member is anchored to the substrate. A second portion of the first MEMS transducing member extends over at least a portion of the cavity and is free to move relative to the cavity. A second MEMS transducing member includes a second size that is smaller than the first size of the first MEMS transducing member. A first portion of the second MEMS transducing member is anchored to the substrate. A second portion of the second MEMS transducing member extends over at least a portion of the cavity and is free to move relative to the cavity. A compliant membrane is positioned in contact with the first and second MEMS transducing members. A first portion of the compliant membrane covers the first and second MEMS transducing members. A second portion of the compliant membrane is anchored to the substrate.

According to another aspect of the invention, an ultrasonic imaging system includes an ultrasonic transmitter and receiver. The ultrasonic transmitter and receiver includes a MEMS composite transducer. The MEMS composite transducer includes a substrate. Portions of the substrate define an outer boundary of a cavity. A first MEMS transducing member includes a first size. A first portion of the first MEMS transducing member is anchored to the substrate. A second portion of the first MEMS transducing member extends over at least a portion of the cavity and is free to move relative to the cavity. A second MEMS transducing member includes a second size that is smaller than the first size of the first MEMS transducing member. A first portion of the second MEMS transducing member is anchored to the substrate. A second portion of the second MEMS transducing member extends over at least a portion of the cavity and is free to move relative to the cavity. A compliant membrane is positioned in contact with the first and second MEMS transducing members. A first portion of the compliant membrane covers the first and second MEMS transducing members. A second portion of the compliant membrane is anchored to the substrate. A first electrical circuit is connected to the first MEMS transducing member. A second electrical circuit is connected to the second MEMS transducing member.

BRIEF DESCRIPTION OF THE DRAWINGS

In the detailed description of the example embodiments of the invention presented below, reference is made to the accompanying drawings, in which:

FIG. 5A is a cross-sectional view of an configuration of a MEMS composite transducer including a plurality of cantilevered beams and a compliant membrane over a cavity;

FIG. 5B is a cross-sectional view of the MEMS composite transducer of FIG. 5A in its deflected state;

FIG. 10A is a cross-sectional view of the MEMS composite transducer of FIG. 9 in its undeflected state;

FIG. 10B is a cross-sectional view of the MEMS composite transducer of FIG. 9 in its deflected state;

DETAILED DESCRIPTION OF THE INVENTION

The present description will be directed in particular to elements forming part of, or cooperating more directly with, apparatus in accordance with the present invention. It is to be understood that elements not specifically shown or described may take various forms well known to those skilled in the art.

Embodiments of the present invention include a variety of types of MEMS composite transducers including a plurality of MEMS transducing members, at least two of which are independently addressable, and a compliant membrane positioned in contact with the plurality of MEMS transducing members. Within the MEMS composite transducer is at least one MEMS transducing member of a larger relative size used as an actuator for ultrasonic wave transmission, and at least one MEMS transducing member of a smaller relative size used as a sensor for ultrasonic echo receiving. It is to be noted that in some definitions of MEMS structures, MEMS components are specified to be between 1 micron and 100 microns in size. Although such dimensions characterize a number of embodiments, it is contemplated that some embodiments will include dimensions outside that range. For a typical ultrasonic transducer array operating in the 1 to 20 MHz range, the pitch of an array of transducers is typically within a range of 20 microns to 1000 microns.

Figures 2A, 2B:
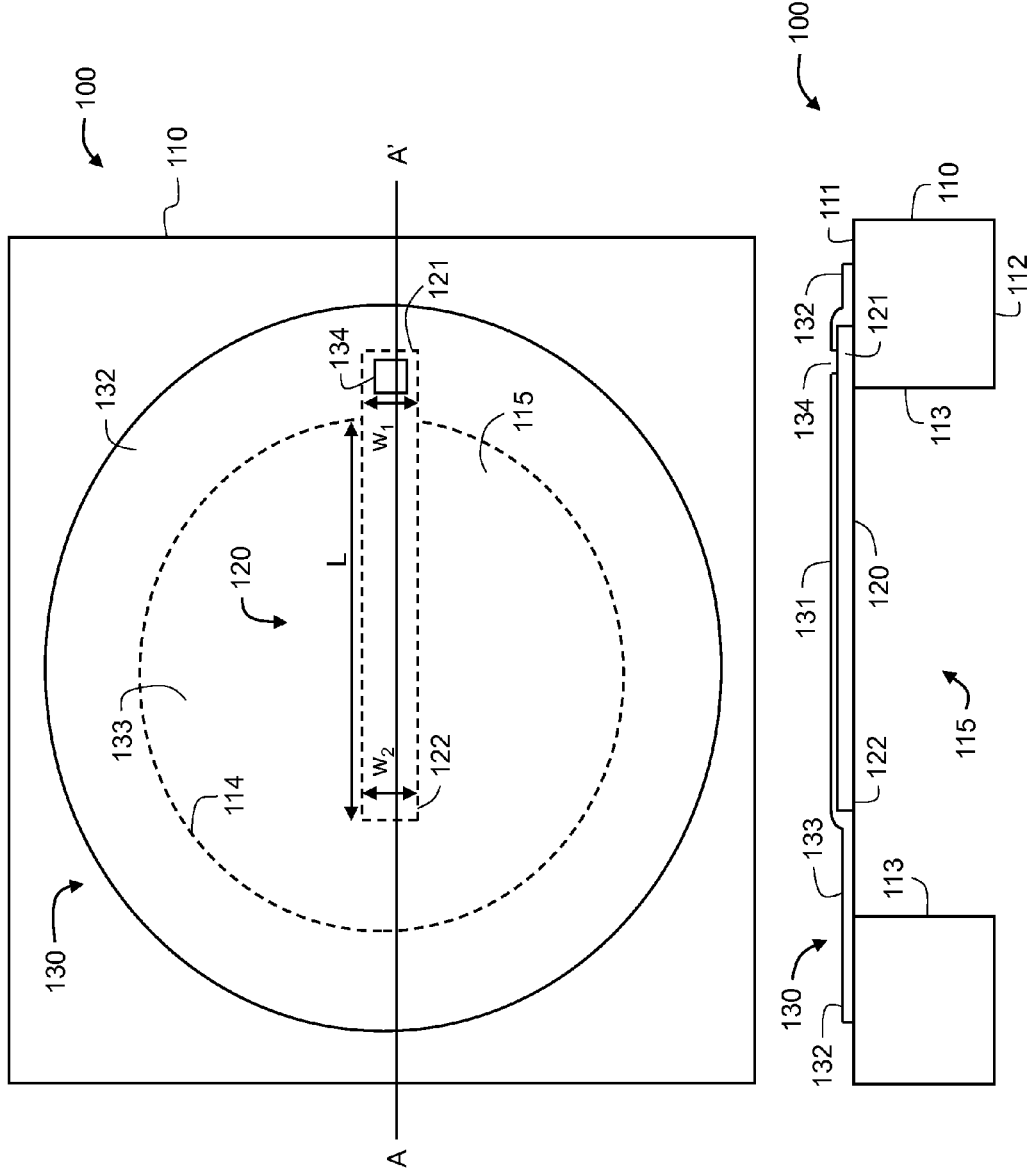
FIG. 2A is a top view and FIG. 2B is a cross-sectional view of a MEMS composite transducer including a cantilevered beam and a compliant membrane over a cavity.

Some general characteristics of a MEMS composite transducer will be explained prior to describing embodiments of the present invention that include a plurality of MEMS transducing members. FIG. 2A shows a top view and FIG. 2B shows a cross-sectional view (along A-A') of a first configuration of a MEMS composite transducer 100, where the MEMS transducing member is a cantilevered beam 120 that is anchored at a first end 121 to a first surface 111 of a substrate 110. Portions 113 of the substrate 110 define an outer boundary 114 of a cavity 115. In the example of FIGS. 2A and 2B, the cavity 115 is substantially cylindrical and is a through hole that extends from a first surface 111 of substrate 110 (to which a portion of the MEMS transducing member is anchored) to a second surface 112 that is opposite first surface 111. Other shapes of cavity 115 are contemplated in which the cavity 115 does not extend all the way to the second surface 112. Still other configurations are contemplated where the cavity shape is not cylindrical with circular symmetry. A portion of cantilevered beam 120 extends over a portion of cavity 115 and terminates at second end 122. The length L of the cantilevered beam extends from the anchored end 121 to the free end 122. Cantilevered beam 120 has a width $w_1$ at first end 121 and a width $w_2$ at second end 122. In the configuration of FIGS. 2A and 2B, $w_1=w_2$, but in some embodiments described below that is not the case. MEMS transducers having an anchored beam cantilevering over a cavity are well known. A feature that distinguishes the MEMS composite transducer 100 from conventional devices is a compliant membrane 130 that is positioned in contact with the cantilevered beam 120 (one example of a MEMS transducing member). Compliant membrane includes a first portion 131 that covers the MEMS transducing member, a second portion 132 that is anchored to first surface 111 of substrate 110, and a third portion 133 that overhangs cavity 115 while not contacting the MEMS transducing member. In a fourth region 134, compliant membrane 130 is removed such that it does not cover a portion of the MEMS transducing member near the first end 121 of cantilevered beam 120, so that electrical contact can be made as is discussed in further detail below. In the configuration shown in FIG. 2B, second portion 132 of compliant membrane 130 that is anchored to substrate 110 is anchored around the outer boundary 114 of cavity 115. In other configurations (not shown), it is contemplated that the second portion 132 would not extend entirely around outer boundary 114.

Figure 3:
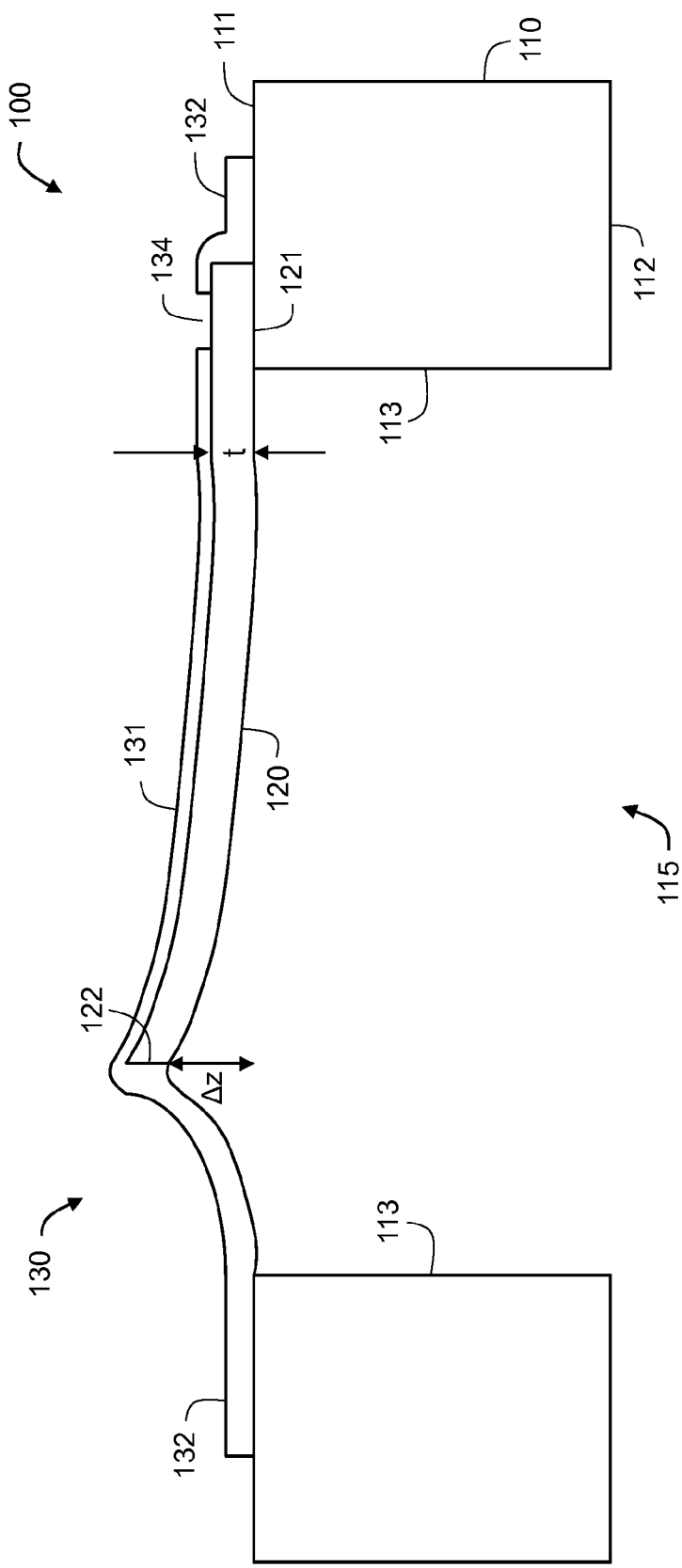
FIG. 3 is a cross-sectional view similar to FIG. 2B, where the cantilevered beam is deflected.

The portion (including end 122) of the cantilevered beam 120 that extends over at least a portion of cavity 115 is free to move relative to cavity 115. A common type of motion for a cantilevered beam is shown in FIG. 3, which is similar to the view of FIG. 2B at higher magnification, but with the cantilevered portion of cantilevered beam 120 deflected upward away by a deflection $\delta=\Delta z$ from the original undeflected position shown in FIG. 2B (the z direction being perpendicular to the x-y plane of the surface 111 of substrate 110). Such a bending motion is provided for example in an actuating mode by a MEMS transducing material (such as a piezoelectric material) that expands or contracts relative to a reference material layer to which it is affixed when an electrical signal is applied, as is discussed in further detail below. When the upward deflection out of the cavity is released (by stopping the electrical signal), the MEMS transducer typically moves from being out of the cavity to into the cavity before it relaxes to its undeflected position. Some types of MEMS transducers have the capability of being driven both into and out of the cavity, and are also freely movable into and out of the cavity.

The compliant membrane 130 is deflected by the MEMS transducer member such as cantilevered beam 120, thereby providing a greater volumetric displacement than is provided by deflecting only cantilevered beam (of a conventional device) that is not in contact with a compliant membrane 130. Desirable properties of compliant membrane 130 are that it have a Young's modulus that is much less than the Young's modulus of typical MEMS transducing materials, that it have a relatively large elongation before breakage, and that it have excellent chemical resistance (for compatibility with MEMS manufacturing processes). Some polymers, including some epoxies, are well adapted to be used as a compliant membrane 130. Examples include TMMR liquid resist or TMMF dry film, both being products of Tokyo Ohka Kogyo Co. The Young's modulus of cured TMMR or TMMF is about 2 GPa, as compared to approximately 70 GPa for a silicon oxide, around 100 GPa for a PZT piezoelectric, around 160 GPa for a platinum metal electrode, and around 300 GPa for silicon nitride. Thus the Young's modulus of the typical MEMS transducing member is at least a factor of 10 greater, and more typically more than a factor of 30 greater than that of the compliant membrane 130. One benefit of a low Young's modulus of the compliant membrane is that this type of design can allow for the compliant membrane 130 to have a negligible effect on the amount of deflection of portion 131 of compliant membrane 130 that covers the MEMS transducing member, but is readily deflected in portion 133 of compliant membrane 130 that is nearby the MEMS transducing member but not directly contacted by the MEMS transducing member. Furthermore, because the Young's modulus of the compliant membrane 130 is much less than that of the typical MEMS transducing member, it has little effect on the resonant frequency of the MEMS composite transducer 100 if the MEMS transducing member (for example, cantilevered beam 120) and the compliant membrane 130 have comparable size. In addition, the elongation before breaking of cured TMMR or TMMF is around 5%, so that it is capable of large deflection without damage.

Figure 4:
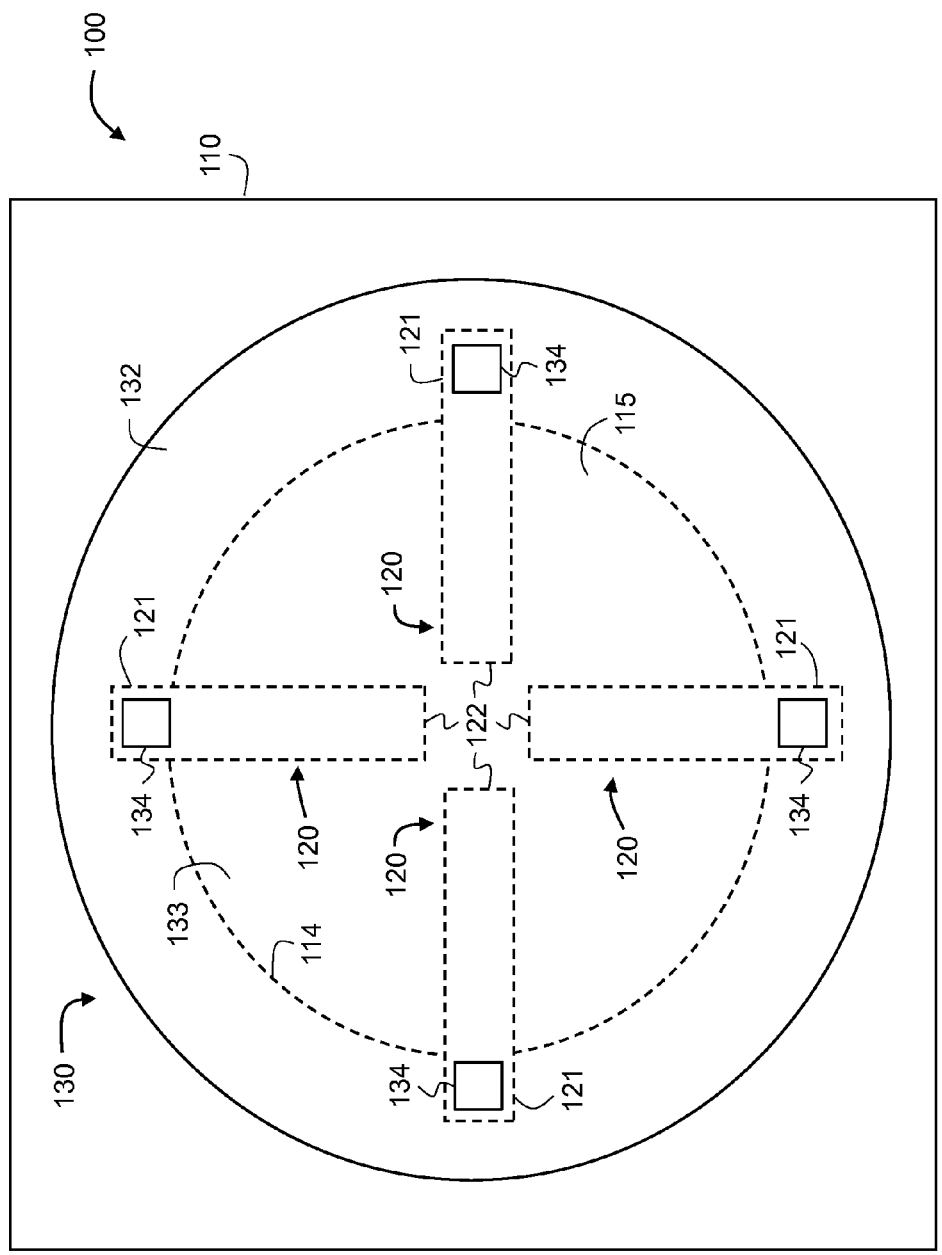
FIG. 4 is a top view of an configuration similar to FIG. 2A, but with a plurality of cantilevered beams over the cavity.

There are many configurations within the family of MEMS composite transducers 100 having a plurality of cantilevered beams 120 as the MEMS transducing members covered by the compliant membrane 130. The different configurations within this family have different amounts of displacement or different resonant frequencies or different amounts of coupling between multiple cantilevered beams 120 extending over a portion of cavity 115, and thereby are well suited to a variety of applications. FIG. 4 shows a top view of a MEMS composite transducer 100 similar to that shown in FIG. 2A, but having four cantilevered beams 120 as the MEMS transducing members, each cantilevered beam 120 including a first end that is anchored to substrate 110, and a second end 122 that is cantilevered over cavity 115. Independent electrical contact can be made to each of the cantilevered beams 120 through the corresponding portion 134 where the compliant membrane 130 is removed. Thus, one or more of the cantilevered beams 120 can be used as actuators and one or more can be used independently as sensors. In many applications, multiple actuator cantilevered beams 120 are electrically connected together, and multiple sensor cantilevered beams 120 are electrically connected together. In these applications it is not necessary to remove compliant membrane 130 in portion 134 over each cantilevered beam 120, but rather over one cantilevered beam 120 for the set of actuators and over another cantilevered beam 120 for the set of sensors.

Figure 1:
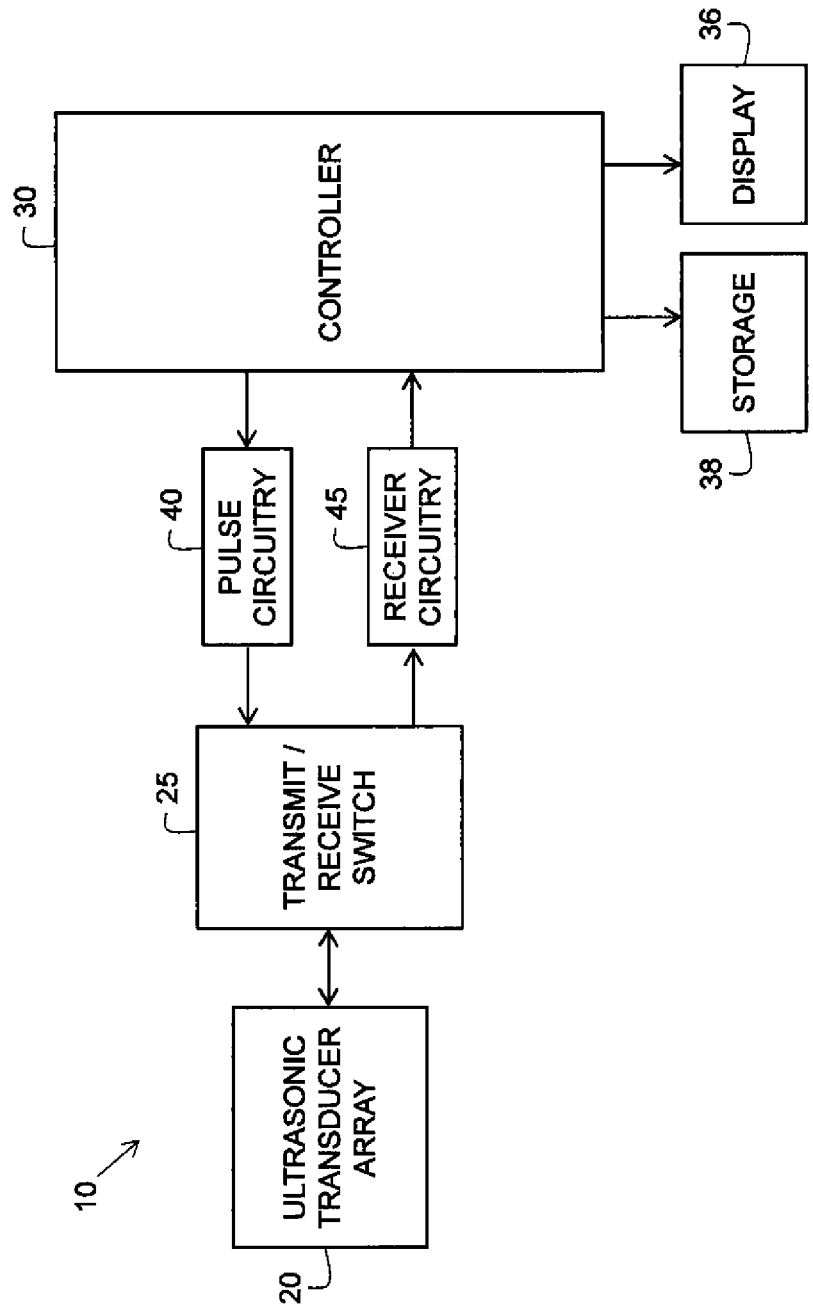
FIG. 1 is a block diagram of a portion of a prior art ultrasonic imaging system.

In the configuration of FIG. 4, the widths $w_1$ (see FIG. 2A) of the first ends 121 of the cantilevered beams 120 are all substantially equal to each other, and the widths $w_2$ (see FIG. 2A) of the second ends 122 of the cantilevered beams 120 are all substantially equal to each other. In addition, $w_1=w_2$ in this configuration. Compliant membrane 130 includes first portions 131 that cover the cantilevered beams 120 (as seen more clearly in the cross-sectional view through a plurality of cantilevered beams 120 in FIG. 5A), a second portion 132 that is anchored to substrate 110, and a third portion 133 that overhangs cavity 115 while not contacting the cantilevered beams 120. The compliant member 130 in this example provides some coupling between the different cantilevered beams 120. In addition, if the cantilevered beams are actuators, the effect of actuating all four cantilevered beams 120 results in an increased volumetric displacement and a more symmetric displacement of the compliant membrane 130 than the single cantilevered beam 120 as seen by comparing FIGS. 1B and 2 with FIGS. 5A and 5B.

Figure 6:
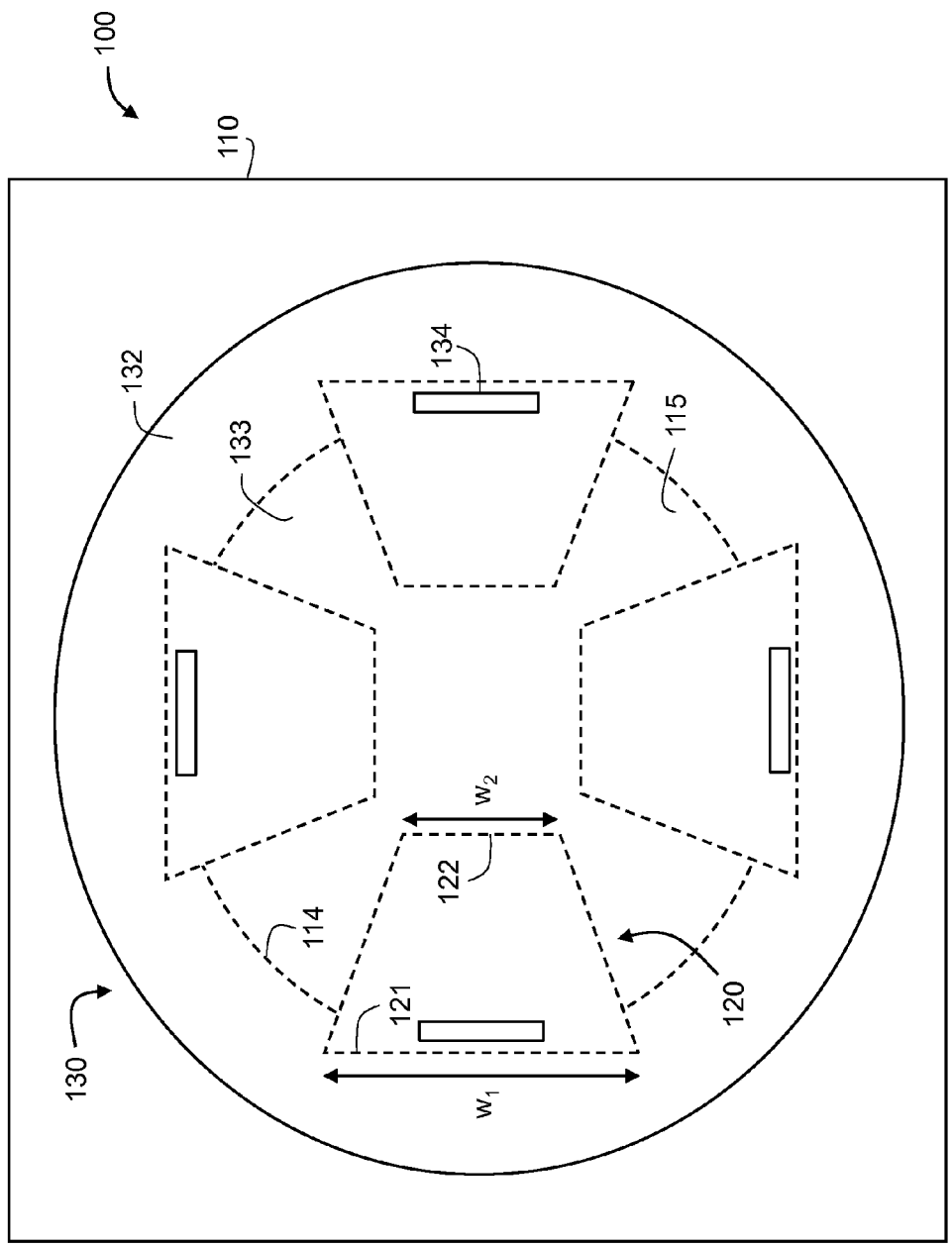
FIG. 6 is a top view of an configuration similar to FIG. 4, but where the widths of the cantilevered beams are larger at their anchored ends than at their free ends.

FIG. 6 shows a configuration similar to FIG. 4, but for each of the four cantilevered beams 120, the width $w_1$ at the anchored end 121 is greater than the width $w_2$ at the cantilevered end 122. For applications where the cantilevered beams 120 are actuators, the effect of actuating the cantilevered beams of FIG. 6 provides a greater volumetric displacement of compliant membrane 130, because a greater portion of the compliant membrane is directly contacted and supported by cantilevered beams 120. As a result the third portion 133 of compliant membrane 130 that overhangs cavity 115 while not contacting the cantilevered beams 120 is smaller in FIG. 6 than in FIG. 4. This reduces the amount of sag in third portion 133 of compliant membrane 130 between cantilevered beams 120 as the cantilevered beams 120 are deflected. A cross-sectional view of the undeflected and deflected states of the configuration of FIG. 6 is similar to that shown in FIGS. 5A and 5B for a plurality of cantilevered beams 120 in contact with a compliant membrane 130.

Figure 7:
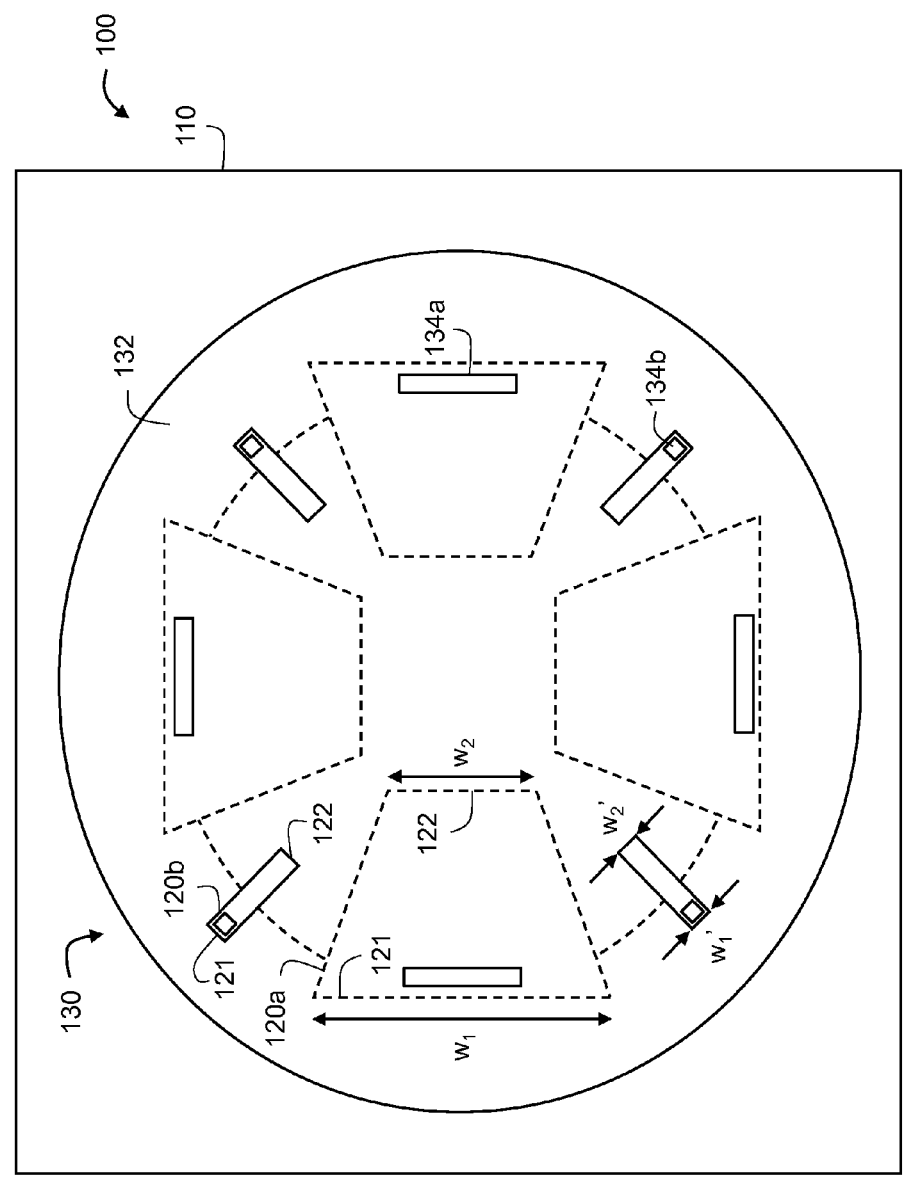
FIG. 7 is a top view of an embodiment of a MEMS composite transducer for use in an ultrasonic transmitter and receiver, having a first group of cantilevered beams and a second group of cantilevered beams of a different size.

FIG. 7 shows a configuration of a MEMS composite transducer 100 that is well-suited as an embodiment of an ultrasonic transmitter and receiver of the present invention. This configuration is similar to FIG. 6, but in addition to the group of cantilevered beams 120a (one example of a plurality of MEMS transducing members) having larger first widths $w_1$ than second widths $w_2$, there is a second group of cantilevered beams 120b (alternatingly arranged between elements of the first group) having first widths $w_1'$ that are equal to second widths $w_2'$. Furthermore, the second group of cantilevered beams 120b are sized smaller than the first group of cantilevered beams 120a, such that the first widths we are smaller than first widths $w_1$, the second widths $w_2'$ are smaller than second widths $w_2$, and the distances (lengths) between the anchored first end 121 and the free second end 122 are also smaller for the group of cantilevered beams 120b. Such an arrangement can be beneficial when the first group of cantilevered beams 120a are used for actuators and the second group of cantilevered beams 120b are used as sensors.

In particular, for an ultrasonic transmitter and receiver, the first group of cantilevered beams 120a are provided with electronic pulses through portions 134a where compliant membrane 130 is removed to allow electrical contact. The first group of relatively large sized cantilevered beams 120a provide a large displacement in the compliant membrane 130. This large displacement is transmitted to a compliant cover layer (not shown) that covers an array of transducers of the type shown for example in FIG. 7. The cover layer provides protection for the array as well as impedance matching to enhance wave transmission efficiency into the object to be imaged. Reflected waves from various structures within the object are transmitted through the cover layer and cause the compliant membranes 130 of the transducers in the array to vibrate at a smaller amplitude than was caused by the electrical pulsing, thus causing the cantilevered beams in first group 120a and second group 120b to vibrate. The piezoelectric transducing material included in the cantilevered beams converts the vibration into an echo electrical signal. The low amplitude echo electrical signals from the second group of relatively smaller sized cantilevered beams 120b are picked up at electrical contacts through portions 134b where compliant membrane 130 is removed.

Figure 8:
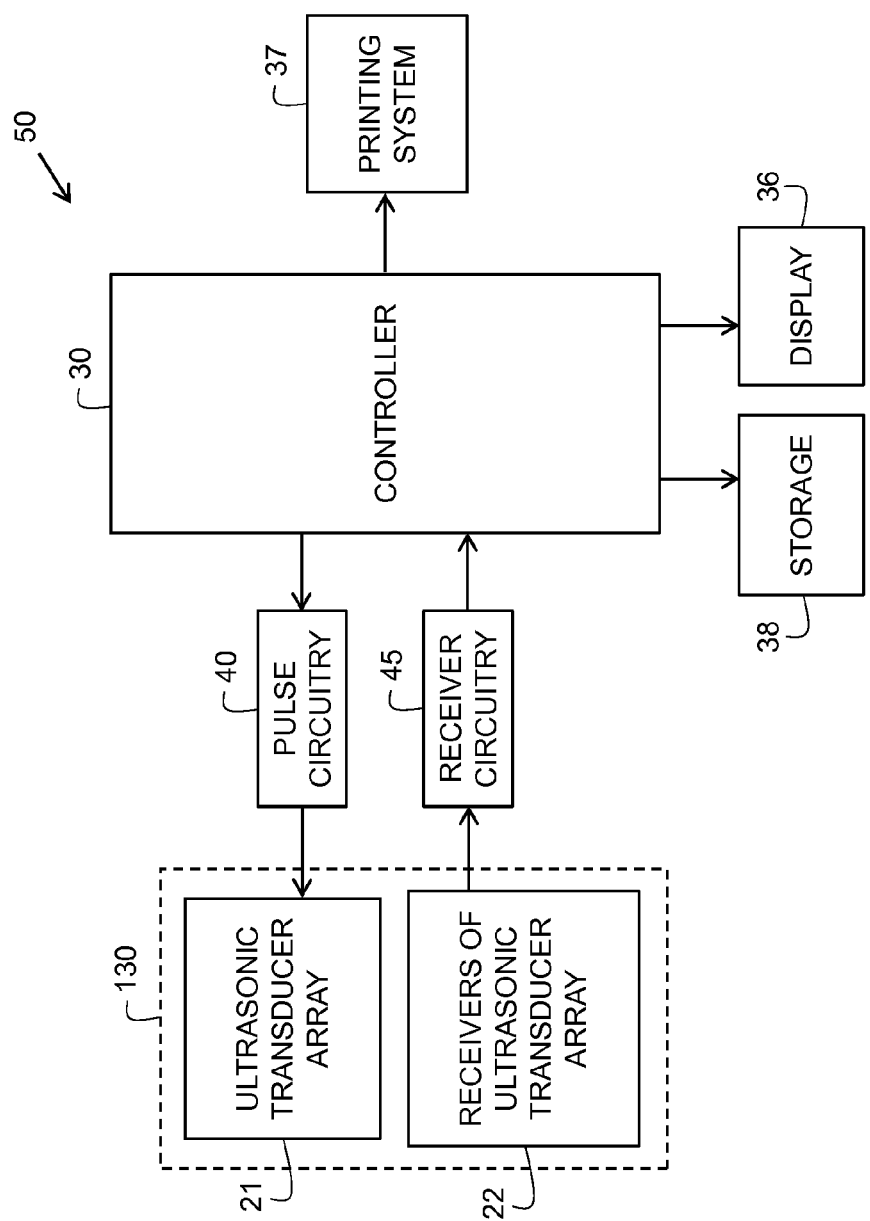
FIG. 8 is a block diagram of a portion of an ultrasonic imaging system according to an embodiment of the invention.

FIG. 8 shows a portion of an ultrasonic imaging system 50 according to an embodiment of the present invention. As seen by comparing FIG. 8 to FIG. 1, the present invention enables elimination of the transmit/receive switch 25 of FIG. 1. This is because pulse circuitry 40 is connected to transmitters of the ultrasonic array 21 (for example, to first group of cantilevered beams 120a shown in FIG. 7) for pulsing with high voltage to actuate them and provide a large volumetric displacement of compliant membrane 130. Because high voltage pulse circuitry 40 is not connected to the receivers of the ultrasonic array 22 (for example, to second group of cantilevered beams 120b), receiving circuitry 45 is electrically isolated from pulsing circuitry 40, and no transmit/receive switch is needed to protect the low noise amplifier in receiving circuitry 45. Instead, receiving circuitry 45 is connected to the receivers of the ultrasonic array 22 (for example, to second group of cantilevered beams 120b shown in FIG. 7) for receiving and then amplifying the low amplitude echo electrical signals. Transmitters of ultrasonic transducer array 21 are mechanically coupled together with receivers of ultrasonic transducer array 22 by compliant membrane 130 (as indicated by the dashed line box in FIG. 8), but transmitters 21 are electrically isolated from receivers 22.

In the configurations described above, the cantilevered beams 120 (one example of the MEMS transducing members) are disposed with substantially radial symmetry around a circular cavity 115. This can be a preferred type of configuration in many embodiments, but other embodiments are contemplated having nonradial symmetry or noncircular cavities.

Figure 9:
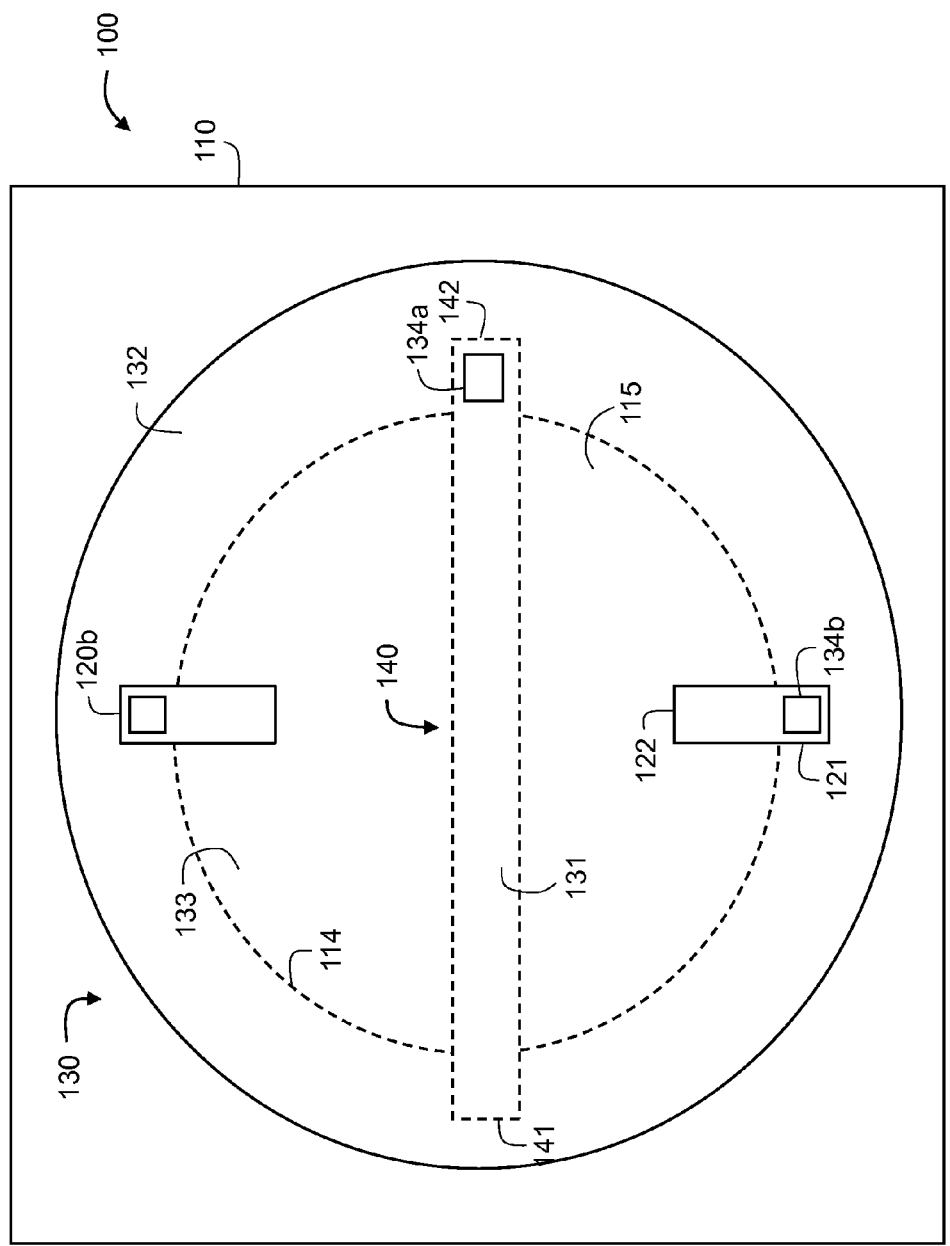
FIG. 9 is a top view of an embodiment of a MEMS composite transducer for use in an ultrasonic transmitter and receiver, including a doubly anchored beam. a compliant membrane and a group of cantilevered beams of a smaller size.

FIG. 9 shows an alternative embodiment of a MEMS composite transducer 100 that can be used in an ultrasonic transmitter and receiver. In the example shown in FIG. 9, a MEMS transducing member for serving as an actuator for transmitting waves is a doubly anchored beam 140 extending across cavity 115 and having a first end 141 and a second end 142 that are each anchored to substrate 110. MEMS transducing members for serving as sensors to receive the reflected waves are cantilevered beams 120b having a smaller size than the doubly anchored beam 140. Cantilevered beams 120b are anchored to substrate 110 at first ends 121 and cantilever over cavity 115 at second ends 122. As in the embodiment of FIG. 7, compliant membrane 130 includes a first portion 131 that covers the MEMS transducing members, a second portion 132 that is anchored to first surface 111 of substrate 110, and a third portion 133 that overhangs cavity 115 while not contacting the MEMS transducing members. In the example of FIG. 9, a portion 134a of compliant membrane 130 is removed over second end 142 of doubly anchored beam 140 in order to make electrical contact to pulse circuitry 40 (FIG. 8), and portions 134b of compliant membrane 130 are removed over first ends 121 of cantilevered beams 120b in order to make electrical contact to receiver circuitry 45.

FIG. 10A shows a cross-sectional view through a doubly anchored beam 140 MEMS composite transducer in its undeflected state. FIG. 10B shows a cross-sectional view of the doubly anchored beam 140 in its deflected state. The portion of doubly anchored beam 140 extending across cavity 115 is deflected up and away from the undeflected position of FIG. 10A, so that it raises up the portion 131 of compliant membrane 130. The maximum deflection at or near the middle of doubly anchored beam 140 is shown as $\delta = \Delta z$.

Figure 11:
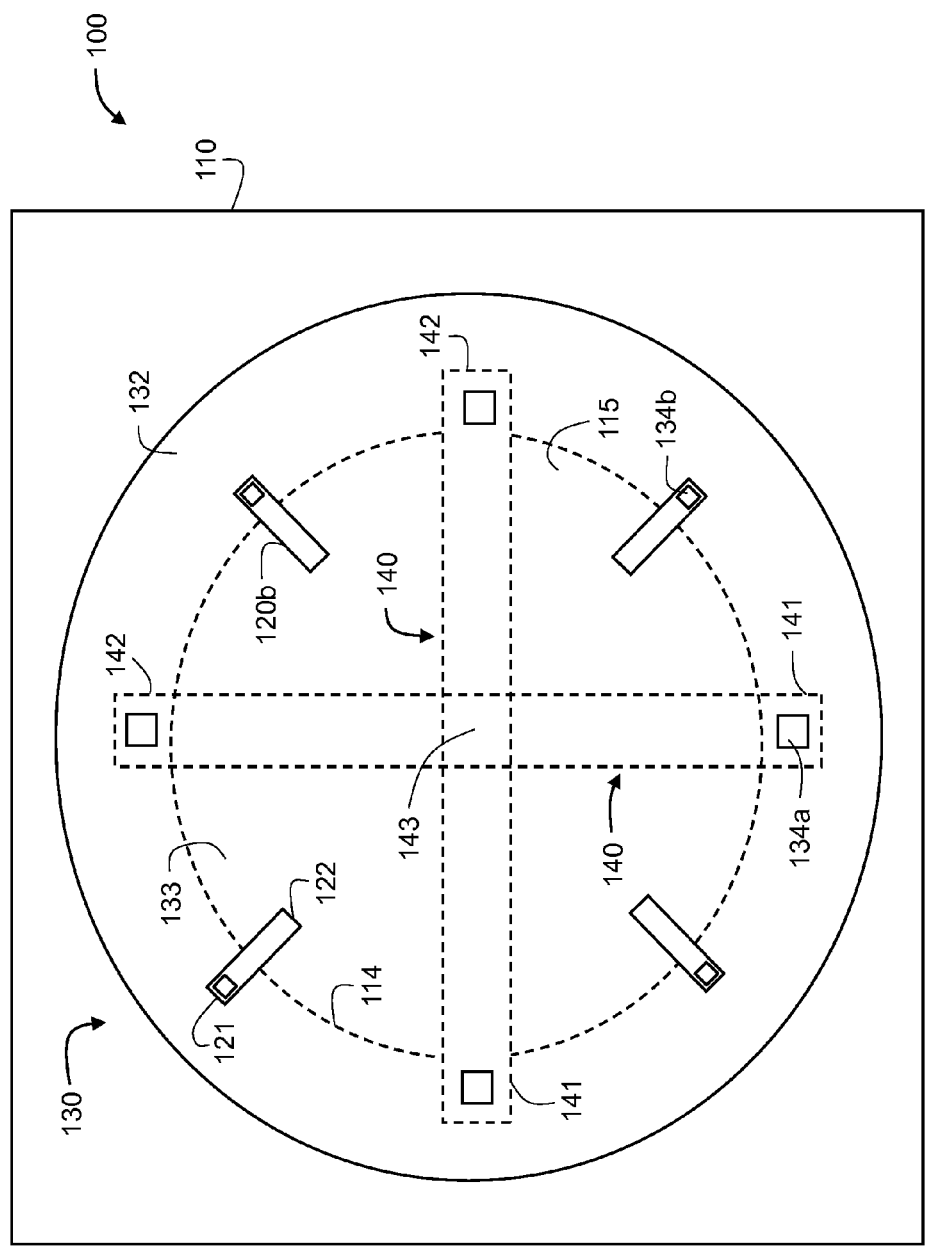
FIG. 11 is a top view of an embodiment of a MEMS composite transducer for use in an ultrasonic transmitter and receiver, including two intersecting doubly anchored beams. a compliant membrane and a group of cantilevered beams of a smaller size.

FIG. 11 shows a top view of another example embodiment of MEMS transducing members that can be used for an ultrasonic transmitter and receiver. It is similar to the configuration of FIG. 9, but with two relatively larger doubly anchored beams 140 anchored to the substrate 110 at their first end 141 and second end 142, and four relatively smaller cantilevered beams 120b anchored to substrate 110 at their first ends 121 and cantilevering over cavity 115 at their second ends 122. In this embodiment both doubly anchored beams 140 are disposed substantially radially across circular cavity 115, and therefore the two doubly anchored beams 140 intersect each other over the cavity at an intersection region 143. Other embodiments are contemplated in which the plurality of doubly anchored beams do not intersect each other or the cavity is not circular.

Figure 12:
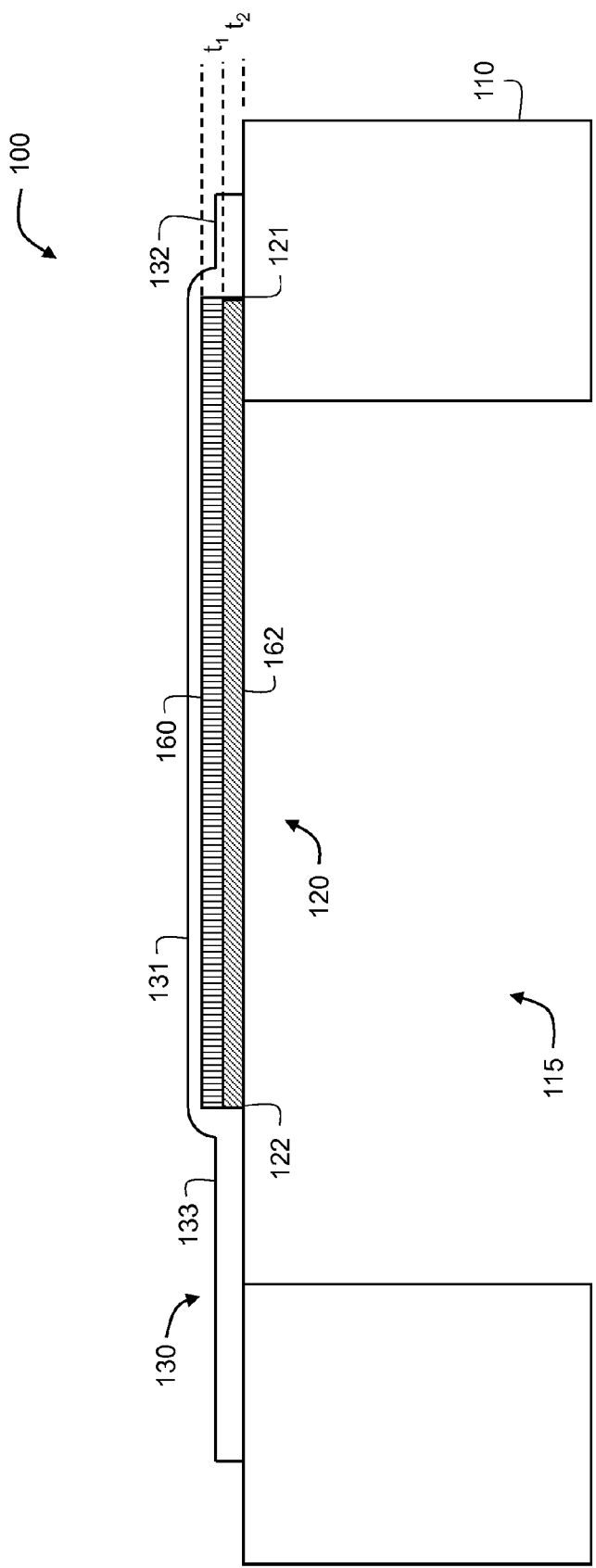
FIG. 12 is a cross-sectional view showing additional structural detail of an embodiment of a MEMS composite transducer including a cantilevered beam.

A variety of transducing mechanisms and materials can be used in the MEMS composite transducer of the present invention, but a preferred MEMS transducing mechanism for use in an ultrasonic transmitter and receiver includes a deflection out of the plane of the undeflected MEMS composite transducer, for example, a bending motion, as shown in FIGS. 5B and 10B. A transducing mechanism including bending is typically provided by a MEMS transducing material 160 in contact with a reference material 162, as shown for the cantilevered beam 120 in FIG. 12. In the example of FIG. 12, the MEMS transducing material 160 is shown on top of reference material 162, but alternatively the reference material 162 can be on top of the MEMS transducing material 160, depending upon whether it is desired to cause bending of the MEMS transducing member (for example, cantilevered beam 120) into the cavity 115 or away from the cavity 115, and whether the MEMS transducing material 160 is caused to expand more than or less than an expansion of the reference material 162.

A preferred MEMS transducing material 160 for an ultrasonic transducer and receiver is a piezoelectric material. Piezoelectric materials are particularly advantageous, as they can be used as both actuators or sensors. In other words, a voltage applied across the piezoelectric MEMS transducing material 160, typically applied to conductive electrodes (not shown) on the two sides of the piezoelectric MEMS transducing material, can cause an expansion or a contraction (depending upon whether the voltage is positive or negative and whether the sign of the piezoelectric coefficient is positive or negative). While the voltage applied across the piezoelectric MEMS transducing material 160 causes an expansion or contraction, the reference material 162 does not expand or contract, thereby causing a deflection into the cavity 115 or away from the cavity 115 respectively. Typically in a piezoelectric composite MEMS transducer, a single polarity of electrical signal would be applied however, so that the piezoelectric material does not tend to become depoled. It is possible to sandwich a reference material 162 between two piezoelectric material layers, thereby enabling separate control of deflection into cavity 115 or away from cavity 115 without depoling the piezoelectric material. Furthermore, an expansion or contraction imparted to the MEMS transducing material 160 produces an electrical signal which can be used to sense motion. There are a variety of types of piezoelectric materials. A family of interest includes piezoelectric ceramics, such as lead zirconate titanate or PZT.

As the MEMS transducing material 160 expands or contracts, there is a component of motion within the plane of the MEMS composite transducer, and there is a component of motion out of the plane (such as bending). Bending motion will be dominant if the Young's modulus and thickness of the MEMS transducing material 160 and the reference material 162 are comparable. In other words, if the MEMS transducing material 160 has a thickness $t_1$ and if the reference material has a thickness $t_2$, then bending motion will tend to dominate if $t_2 > 0.5 t_1$ and $t_2 < 2 t_1$, assuming comparable Young's moduli.

Referring again to FIGS. 7 to 9 and 11, an embodiment of the ultrasonic imaging system 50 is described in further detail. An ultrasonic transmitter and receiver are provided including an array (a plurality) of MEMS composite transducers 100 on a substrate 110. Each MEMS composite transducer includes a cavity 115. A first MEMS transducing member (for example, a cantilevered beam 120a or a doubly anchored beam 140) of a first size has a first portion that is anchored on the substrate 110 and a second portion that extends over at least a portion of the cavity 115. The second portion of the first MEMS transducing member is free to move relative to the cavity. Likewise, there is a second MEMS transducing member of a second size that is smaller than the first size of the first MEMS transducing member. The second MEMS transducing member also includes an anchored first portion and a second portion that extends over at least a portion of cavity 115. A compliant membrane 130 is positioned in contact with the first and second MEMS transducing members. First portions 131 of compliant membrane 130 cover the first and second MEMS transducing members, and a second portion 132 of compliant membrane 130 is anchored to substrate 110.

A first electrical circuit (pulse circuitry 40) is connected to the first MEMS transducing member, and a second electrical circuit (receiver circuitry 45) is connected to the second MEMS transducing member. Pulse circuitry 40 includes a voltage source, and also includes a pulse generator. In some embodiments the maximum voltage of the voltage source is up to 200V. In other embodiments the maximum voltage of the voltage source is somewhat lower, for example 20V. Receiver circuitry 45 includes a low noise amplifier. Controller 30 includes signal processing circuitry to process signals from the low noise amplifier. Controller 30 is configured (includes hardware, or software, or firmware, or combination thereof) to transform the processed signals into a digital image that can be viewed on a display 36, printed on a printing system 37, or saved in storage 38. Storage can include any of a wide range of storage types for digital data including optical storage media, magnetic storage media, electronic memory, and the like.

Figure 13:
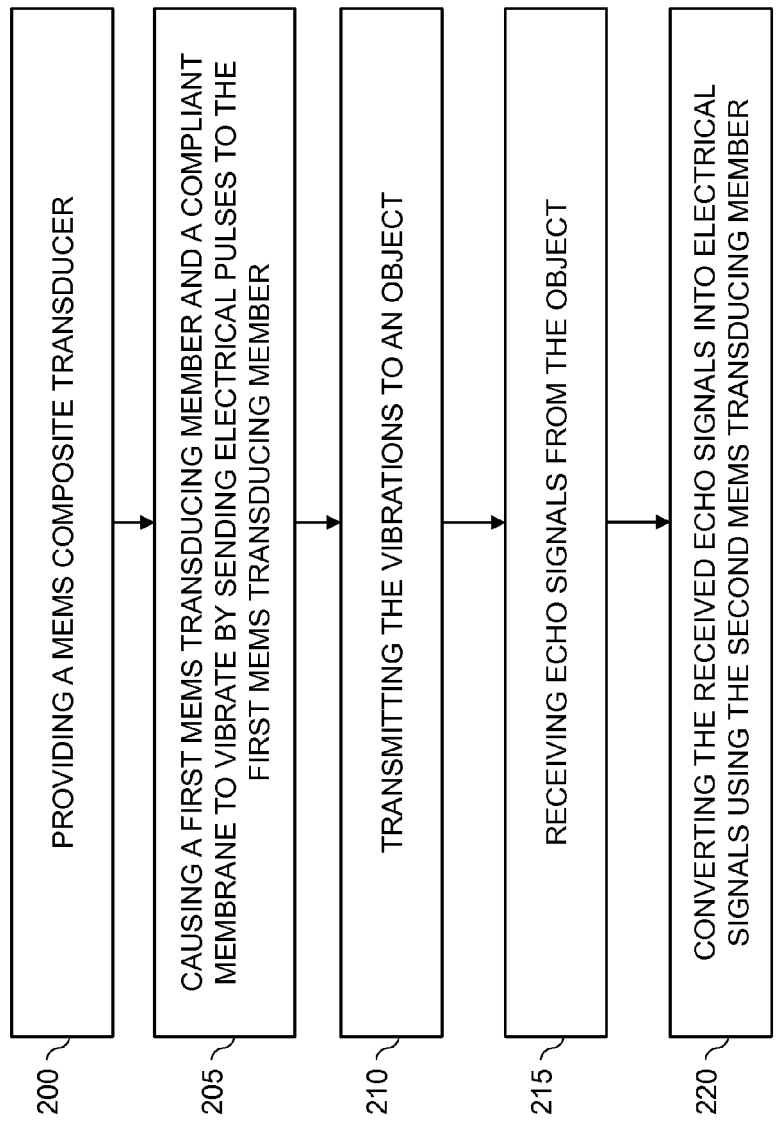
FIG. 13 is a block diagram describing an example embodiment of a method of operating an ultrasonic transmitter and receiver.

A method of operating an ultrasonic transmitter and receiver of the type described above in an ultrasonic imaging system is described with reference to FIG. 13. A MEMS composite transducer is provided in step 200. Controller 30 controls the timing of electrical pulses to be sent from pulsing circuitry 40 to the first transducing member(s) (for example, cantilevered beam(s) 120a or doubly anchored beam(s) 140) in an array of MEMS composite transducers, causing the first transducing members and the compliant membrane 130 to vibrate in step 205. The electrical pulses are typically voltage pulses having an amplitude typically between 20V and 200V and a pulse width less than 1 microsecond, with a delay time of less than 1 microsecond between a first electrical pulse and a second electrical pulse. The relative timing of the pulsing for different MEMS composite transducers in the array is typically phased to provide an arc-shaped wave front of ultrasonic waves. The vibrations of the first MEMS transducing member(s) are transmitted to an object to be imaged in step 210. Echo signals (the reflected waves) are received from the object in step 215, and the received echo signals are converted into echo electrical signals by the second MEMS transducing member(s) in step 220, which are amplified by a low noise amplifier in the receiving circuitry 45. The amplified signals from the second MEMS transducing member(s) are sent to the controller 30 for signal processing. Signals from a plurality of MEMS composite transducers 100 in the ultrasonic transmitter and receiver array are processed to form a digital image of the object. The image can be viewed on a display 36, printed on a printing system 37 or saved in storage 38.

In order to transmit the vibrations to and from the object, an ultrasonic transmitter and receiver array probe is typically held in contact with the object to be imaged. The probe typically includes an impedance matching and protective cover layer over the array. In some embodiments the cover layer can be formed of a polymer such as parylene. Particularly for medical ultrasonography implementations, where the object is typically alive, a transmission enhancing material such as a gel is applied to the object in the region where probe contact will be made.

The invention has been described in detail with particular reference to certain preferred embodiments thereof, but it will be understood that variations and modifications can be effected within the scope of the invention.

PARTS LIST

- 10 Ultrasonic imaging system (prior art)
- 20 Ultrasonic transducer array (prior art)
- 21 Transmitters
- 22 Receivers
- 25 Transmit/receive switch (prior art)
- 30 Controller
- 36 Display
- 37 Printing system
- 38 Storage
- 40 Pulse circuitry
- 45 Receiver circuitry
- 50 Ultrasonic imaging system
- 100 MEMS composite transducer
- 110 Substrate
- 111 First surface of substrate
- 112 Second surface of substrate
- 113 Portions of substrate (defining outer boundary of cavity)
- 114 Outer boundary
- 115 Cavity
- 120 Cantilevered beam
- 120a Cantilevered beams of first group (actuators)
- 120b Cantilevered beams of second group (sensors)
- 121 Anchored end (of cantilevered beam)
- 122 Cantilevered end (of cantilevered beam)
- 130 Compliant membrane
- 131 Covering portion of compliant membrane
- 132 Anchoring portion of compliant membrane
- 133 Portion of compliant membrane overhanging cavity
- 134 Portion where compliant membrane is removed
- 140 Doubly anchored beam
- 141 First anchored end
- 142 Second anchored end
- 143 Intersection region
- 160 MEMS transducing material
- 162 Reference material
- 200 providing MEMS composite transducer
- 205 Vibration of first MEMS transducing member and compliant membrane
- 210 Vibration transmission
- 215 Echo signals received
- 220 Second MEMS transducing member converts echo signals into electrical signals

The invention claimed is:

1. An ultrasonic transmitter and receiver comprising:
a MEMS composite transducer comprising
a substrate, portions of the substrate defining an outer boundary of a cavity;
a first MEMS transducing member including a first size, a first portion of the first MEMS transducing member being anchored to the substrate, a second portion of the first MEMS transducing member extending over at least a portion of the cavity, the second portion of the first MEMS transducing member being free to move relative to the cavity;
a second MEMS transducing member including a second size smaller than the first size, a first portion of the second MEMS transducing member being anchored to the substrate, a second portion of the second MEMS transducing member extending over at least a portion of the cavity, the second portion of the second MEMS transducing member being free to move relative to the cavity; and
a compliant membrane positioned in contact with the first and second MEMS transducing members, a first portion of the compliant membrane covering the first and second MEMS transducing members, and a second portion of the compliant membrane being anchored to the substrate.

2. The ultrasonic transmitter and receiver of claim 1, wherein the compliant membrane is anchored to the substrate around the outer boundary of the cavity.

3. The ultrasonic transmitter and receiver of claim 1, the first and second MEMS transducing members each comprising a beam having a first end and a second end, wherein the first end is anchored to the substrate and the second end cantilevers over the cavity.

4. The ultrasonic transmitter and receiver of claim 3, the beam of the first MEMS transducing member including a first width at its first end and a second width at its second end, wherein the first width is greater than the second width.

5. The ultrasonic transmitter and receiver of claim 3, the beam of the first MEMS transducing member including a first width at its first end and a second width at its second end, and the beam of the second MEMS transducing member including a third width at its first end and a fourth width at its second end, wherein the third width is smaller than the first width.

6. The ultrasonic transmitter and receiver of claim 3, the beam of the first MEMS transducing member including a first width at its first end and a second width at its second end, and the beam of the second MEMS transducing member including a third width at its first end and a fourth width at its second end, wherein the fourth width is smaller than the second width.

7. The ultrasonic transmitter and receiver of claim 3, the beam of the first MEMS transducing member including a first length, and the beam of the second MEMS transducing member including a second length, wherein the second length is smaller than the first length.

8. The ultrasonic transmitter and receiver of claim 1, the first MEMS transducing member being one of a first plurality of MEMS transducing members each having a first size, and the second MEMS transducing member being one of a second plurality of MEMS transducing members each having a second size smaller than the first size.

9. The ultrasonic transmitter and receiver of claim 8, a first end of each of the first plurality of MEMS transducing members and a first end of each of the second plurality of MEMS transducing members being anchored to the substrate, and a second end of each of the first plurality of MEMS transducing members and a second end of each of the second plurality of MEMS transducing members being cantilevered over the cavity.

10. The ultrasonic transmitter and receiver of claim 1, the first MEMS transducing member comprising a beam having a first end and a second end, wherein the first end and the second end are anchored to the substrate.

11. The ultrasonic transmitter and receiver of claim 10, the second MEMS transducing member comprising a beam having a first end and a second end, wherein the first end of the beam of the second MEMS transducing member is anchored to the substrate and the second end cantilevers over the cavity.

12. The ultrasonic transmitter and receiver of claim 1, the first MEMS transducing member being a first of a plurality of MEMS transducing members each comprising a beam having a first end and a second end, wherein the first end and the second end are anchored to the substrate, and wherein at least two of the beams anchored at both the first and second end intersect each other over the cavity.

13. The ultrasonic transmitter and receiver of claim 1, wherein a shape of the cavity is substantially cylindrical.

14. The ultrasonic transmitter and receiver of claim 1, wherein the first MEMS transducing member and the second MEMS transducing member each comprise a piezoelectric material.

15. The ultrasonic transmitter and receiver of claim 14, wherein the piezoelectric material comprises a piezoelectric ceramic.

16. The ultrasonic transmitter and receiver of claim 15, wherein the piezoelectric ceramic comprises lead zirconate titanate.

17. The ultrasonic transmitter and receiver of claim 1, wherein the compliant membrane comprises a polymer.

18. The ultrasonic transmitter and receiver of claim 17, wherein the polymer comprises an epoxy.

19. The ultrasonic transmitter and receiver of claim 1, the first MEMS transducing member and the second MEMS transducing member each having a first Young's modulus and the compliant membrane having a second Young's modulus, wherein the first Young's modulus is at least 10 times greater than the second Young's modulus.

20. An ultrasonic imaging system comprising:
an ultrasonic transmitter and receiver comprising:
a MEMS composite transducer comprising
a substrate, portions of the substrate defining an outer boundary of a cavity;
a first MEMS transducing member including a first size, a first portion of the first MEMS transducing member being anchored to the substrate, a second portion of the first MEMS transducing member extending over at least a portion of the cavity, the second portion of the first MEMS transducing member being free to move relative to the cavity;
a second MEMS transducing member including a second size smaller than the first size, a first portion of the second MEMS transducing member being anchored to the substrate, a second portion of the second MEMS transducing member extending over at least a portion of the cavity, the second portion of the second MEMS transducing member being free to move relative to the cavity; and
a compliant membrane positioned in contact with the first and second MEMS transducing members, a first portion of the compliant membrane covering the first and second MEMS transducing members, and a second portion of the compliant membrane being anchored to the substrate;
a first electrical circuit connected to the first MEMS transducing member; and
a second electrical circuit connected to the second MEMS transducing member.

21. The ultrasonic imaging system of claim 20, wherein the first electrical circuit includes a voltage source greater than 20 volts.

22. The ultrasonic imaging system of claim 21, wherein the first electrical circuit includes a pulse generator.

23. The ultrasonic imaging system of claim 20, wherein the second electrical circuit includes a low noise amplifier.

24. The ultrasonic imaging system of claim 23 further comprising signal processing circuitry to process signals from the low noise amplifier.

25. The ultrasonic imaging system of claim 24 further comprising a display for viewing an image corresponding to the processed signals.

26. The ultrasonic imaging system of claim 24 further comprising a printing system to provide a printed image corresponding to the processed signals.

27. The ultrasonic imaging system of claim 24 further comprising a storage medium for storing an image corresponding to the processed signals.

28. The ultrasonic imaging system of claim 20, wherein the MEMS composite transducer is one of a plurality of MEMS composite transducers.

* * * * *